United States Patent
Bernard et al.

(10) Patent No.: US 10,631,996 B2
(45) Date of Patent: Apr. 28, 2020

(54) EXPANSIBLE INTERSOMATIC CAGE

(71) Applicant: LDR Medical, S.A.S., Sainte-Savine (FR)

(72) Inventors: Pierre Bernard, Bordeaux (FR); Hervé Chataigner, Boussieres (FR); Craig Chebuhar, Marietta, GA (US); Alexander Kirgis, Krailling (DE); Ross Sherban, Clarence, NY (US); Samuel Lequette, Pessac (FR); Emmanuel Bougere, Bordeaux (FR); Aymeric Fresneau, Bordeaux (FR); Nicolas Roche, Saint Medard en Jalles (FR)

(73) Assignee: LDR Medical, S.A.S., Sainte-Savine (FR)

( * ) Notice: Subject to any disclaimer, the term of this patent is extended or adjusted under 35 U.S.C. 154(b) by 0 days.

(21) Appl. No.: 15/796,733

(22) Filed: Oct. 27, 2017

(65) Prior Publication Data

US 2018/0116811 A1 May 3, 2018

(30) Foreign Application Priority Data

Oct. 27, 2016 (FR) ...................................... 16 60474

(51) Int. Cl.
- *A61F 2/44* (2006.01)
- *A61F 2/30* (2006.01)
- *A61F 2/46* (2006.01)

(52) U.S. Cl.
CPC .......... *A61F 2/442* (2013.01); *A61F 2/30767* (2013.01); *A61F 2/4455* (2013.01);
(Continued)

(58) Field of Classification Search
CPC .. A61F 2/442–4425; A61F 2/446–4465; A61F 2002/30537–30545
See application file for complete search history.

(56) References Cited

U.S. PATENT DOCUMENTS 5,171,278 A * 12/1992 Pisharodi ................ A61F 2/442
128/898
7,879,098 B1 * 2/2011 Simmons, Jr. ........ A61F 2/4465
623/17.11
(Continued)

FOREIGN PATENT DOCUMENTS

WO WO-2018078453 A1 5/2018

OTHER PUBLICATIONS

"International Application Serial No. PCT/IB2017/001494, International Search Report dated Feb. 13, 2018", 3 pgs.
(Continued)

*Primary Examiner* — Jacqueline T Johanas
*Assistant Examiner* — Michelle C Eckman
(74) *Attorney, Agent, or Firm* — Schwegman Lundberg & Woessner, P.A.

(57) ABSTRACT

An expansible intervertebral implant is disclosed, various embodiments of which comprise an elongated body along a longitudinal axis comprised between a proximal end and a distal end, a flexible arm mounted in the vicinity of the distal end of the longitudinal body and movable between: a folded-back position with the arm substantially parallel to the axis, and a deployed position with the arm not parallel to the axis and away from the body to expand said implant along an axis, by assuming the general shape of a circular arc, a means for deployment of said flexible arm for deploying the latter from the folded-back position to the deployed position, by the sliding of a proximal portion of said flexible arm with respect to the body inducing an increase in the space occupied by the implant, greater than the space of the implant in the folded-back position.

15 Claims, 7 Drawing Sheets

(52) U.S. Cl.
CPC ..... *A61F 2/4611* (2013.01); *A61F 2002/3006* (2013.01); *A61F 2002/30112* (2013.01); *A61F 2002/30329* (2013.01); *A61F 2002/30537* (2013.01); *A61F 2002/30556* (2013.01)

(56) References Cited

U.S. PATENT DOCUMENTS

| | | | |
|---|---|---|---|
| 8,556,979 B2* | 10/2013 | Glerum | A61F 2/4455 606/279 |
| 9,622,874 B2* | 4/2017 | McCormack | A61F 2/442 |
| 9,795,493 B1* | 10/2017 | Bannigan | A61F 2/4455 |
| 9,883,953 B1* | 2/2018 | To | A61F 2/446 |
| 10,105,238 B2* | 10/2018 | Koch | A61F 2/4455 |
| 2005/0182417 A1* | 8/2005 | Pagano | A61B 17/025 606/92 |
| 2005/0278028 A1* | 12/2005 | Mujwid | A61F 2/446 623/17.13 |
| 2006/0167547 A1* | 7/2006 | Suddaby | A61F 2/446 623/17.11 |
| 2007/0073398 A1* | 3/2007 | Fabian | A61F 2/442 623/17.11 |
| 2007/0142915 A1* | 6/2007 | Altarac | A61B 17/7065 623/17.11 |
| 2007/0219634 A1* | 9/2007 | Greenhalgh | A61F 2/446 623/17.16 |
| 2007/0233244 A1* | 10/2007 | Lopez | A61F 2/4425 623/17.11 |
| 2007/0233261 A1* | 10/2007 | Lopez | A61F 2/4425 623/17.13 |
| 2007/0282449 A1* | 12/2007 | de Villiers | A61F 2/4425 623/17.15 |
| 2008/0133014 A1* | 6/2008 | Gately | A61F 2/4425 623/17.16 |
| 2008/0183204 A1* | 7/2008 | Greenhalgh | A61B 17/8858 606/198 |
| 2008/0319549 A1* | 12/2008 | Greenhalgh | A61B 17/025 623/17.16 |
| 2009/0270873 A1* | 10/2009 | Fabian | A61F 2/442 606/99 |
| 2010/0010633 A1* | 1/2010 | Kohm | A61F 2/447 623/17.16 |
| 2010/0016973 A1* | 1/2010 | de Villiers | A61F 2/4425 623/17.16 |
| 2010/0069912 A1* | 3/2010 | McCormack | A61B 17/025 606/90 |
| 2010/0161062 A1* | 6/2010 | Foley | A61F 2/4455 623/17.16 |
| 2010/0185291 A1* | 7/2010 | Jimenez | F16C 11/12 623/17.16 |
| 2010/0286783 A1* | 11/2010 | Lechmann | A61F 2/3094 623/17.12 |
| 2011/0066231 A1* | 3/2011 | Cartledge | A61B 17/068 623/2.11 |
| 2011/0276141 A1* | 11/2011 | Caratsch | A61F 2/4455 623/17.16 |
| 2012/0004732 A1* | 1/2012 | Goel | A61F 2/4425 623/17.16 |
| 2012/0071977 A1* | 3/2012 | Oglaza | A61B 17/7065 623/17.11 |
| 2012/0123546 A1* | 5/2012 | Medina | A61F 2/442 623/17.16 |
| 2012/0215316 A1* | 8/2012 | Mohr | A61F 2/442 623/17.16 |
| 2012/0232665 A1* | 9/2012 | Godara | A61F 2/442 623/17.16 |
| 2012/0271422 A1* | 10/2012 | Miller | A61F 2/447 623/17.16 |
| 2013/0012994 A1* | 1/2013 | McCormack | A61B 17/025 606/247 |
| 2013/0110239 A1* | 5/2013 | Siegal | A61B 17/7098 623/17.16 |
| 2013/0144388 A1* | 6/2013 | Emery | A61B 17/025 623/17.16 |
| 2013/0144391 A1* | 6/2013 | Siegal | A61F 2/442 623/17.16 |
| 2013/0166027 A1* | 6/2013 | Bellas | A61F 2/442 623/17.16 |
| 2013/0166030 A1* | 6/2013 | Biedermann | A61F 2/442 623/17.16 |
| 2013/0190876 A1* | 7/2013 | Drochner | A61F 2/442 623/17.16 |
| 2013/0190877 A1* | 7/2013 | Medina | A61F 2/4455 623/17.16 |
| 2013/0304213 A1* | 11/2013 | Aflatoon | A61F 2/4455 623/17.16 |
| 2013/0310939 A1* | 11/2013 | Fabian | A61F 2/442 623/17.16 |
| 2013/0317617 A1* | 11/2013 | Mayer | A61F 2/442 623/17.16 |
| 2014/0012383 A1 | 1/2014 | Triplett et al. | |
| 2014/0039622 A1* | 2/2014 | Glerum | A61F 2/442 623/17.15 |
| 2014/0100662 A1* | 4/2014 | Patterson | A61F 2/4455 623/17.16 |
| 2014/0172106 A1* | 6/2014 | To | A61F 2/442 623/17.16 |
| 2014/0188224 A1* | 7/2014 | Dmuschewsky | A61F 2/442 623/17.16 |
| 2014/0277471 A1* | 9/2014 | Gray | A61F 2/442 623/17.15 |
| 2015/0012098 A1* | 1/2015 | Eastlack | A61F 2/447 623/17.15 |
| 2015/0018954 A1* | 1/2015 | Loebl | A61F 2/4425 623/17.16 |
| 2015/0045893 A1* | 2/2015 | Dinville | A61F 2/44 623/17.16 |
| 2015/0073552 A1* | 3/2015 | To | A61F 2/4611 623/17.15 |
| 2015/0148908 A1* | 5/2015 | Marino | A61F 2/4455 623/17.16 |
| 2015/0173913 A1* | 6/2015 | Lechmann | A61F 2/446 623/17.16 |
| 2015/0209152 A1* | 7/2015 | Patterson | A61F 2/4455 623/17.13 |
| 2015/0230929 A1* | 8/2015 | Lorio | A61F 2/442 623/17.16 |
| 2015/0272743 A1* | 10/2015 | Jimenez | A61F 2/447 623/17.16 |
| 2015/0282797 A1* | 10/2015 | O'Neil | A61B 17/025 606/279 |
| 2016/0120660 A1* | 5/2016 | Melkent | A61F 2/4455 623/17.16 |
| 2016/0166396 A1* | 6/2016 | McClintock | A61F 2/30771 623/17.16 |
| 2016/0206439 A1* | 7/2016 | To | A61F 2/442 |
| 2016/0278935 A1* | 9/2016 | Overes | A61F 2/442 |
| 2016/0324654 A1* | 11/2016 | Loebl | A61F 2/4455 |
| 2016/0361177 A1* | 12/2016 | Biedermann | A61F 2/446 |
| 2017/0000622 A1* | 1/2017 | Thommen | A61F 2/4425 |
| 2017/0042695 A1* | 2/2017 | Foley | A61F 2/4455 |
| 2017/0056197 A1* | 3/2017 | Weiman | A61F 2/447 |
| 2017/0105844 A1* | 4/2017 | Kuyler | A61F 2/447 |
| 2017/0119542 A1* | 5/2017 | Logan | A61F 2/442 |
| 2017/0119544 A1* | 5/2017 | Dewey | A61F 2/4425 |
| 2017/0202679 A1* | 7/2017 | Butler | A61F 2/4465 |
| 2017/0216045 A1* | 8/2017 | Dewey | A61F 2/447 |
| 2017/0216051 A1* | 8/2017 | Dewey | A61F 2/4455 |
| 2017/0231778 A1* | 8/2017 | Overes | A61F 2/4455 623/17.16 |
| 2017/0312090 A1* | 11/2017 | Sharabani | A61F 2/44 |
| 2017/0312092 A1* | 11/2017 | Link | A61F 2/4455 |
| 2017/0319352 A1* | 11/2017 | Dewey | A61F 2/4425 |
| 2017/0325967 A1* | 11/2017 | Link | A61F 2/4455 |
| 2017/0340777 A1* | 11/2017 | Ma | A61L 27/06 |
| 2017/0367842 A1* | 12/2017 | Predick | A61F 2/44 |
| 2017/0367843 A1* | 12/2017 | Eisen | A61F 2/30734 |
| 2018/0000606 A1* | 1/2018 | Hessler | A61F 2/4425 |
| 2018/0014944 A1* | 1/2018 | Davis | A61F 2/447 |

(56) References Cited

U.S. PATENT DOCUMENTS

| | | | |
|---|---|---|---|
| 2018/0078384 A1* | 3/2018 | Suddaby | A61F 2/4425 |
| 2018/0116811 A1* | 5/2018 | Bernard | A61F 2/30767 |
| 2018/0116812 A1* | 5/2018 | Bernard | A61F 2/4455 |
| 2018/0116815 A1* | 5/2018 | Kuyler | A61F 2/447 |
| 2018/0125671 A1* | 5/2018 | Bernard | A61F 2/30771 |
| 2018/0185164 A1* | 7/2018 | Sharabani | A61F 2/4425 |
| 2018/0193164 A1* | 7/2018 | Shoshtaev | A61F 2/4455 |
| 2018/0228617 A1* | 8/2018 | Srour | A61F 2/442 |
| 2018/0311047 A1* | 11/2018 | Liu | A61F 2/442 |
| 2018/0311048 A1* | 11/2018 | Glerum | A61F 2/4684 |
| 2018/0318101 A1* | 11/2018 | Engstrom | A61F 2/442 |

OTHER PUBLICATIONS

"International Application Serial No. PCT/IB2017/001494, Written Opinion dated Feb. 13, 2018", 5 pgs.

* cited by examiner

EXPANSIBLE INTERSOMATIC CAGE

CROSS-REFERENCE TO RELATED APPLICATIONS

This application claims priority under 35 U.S.C. § 119 to French Patent Application No. FR1660474 filed in FRANCE on Oct. 27, 2016, which is incorporated herein by reference.

BACKGROUND

The present application relates to the field of intervertebral cages and generally to the field of implants intended to be implanted between two adjacent verterbrae, to at least partly supplant an intervertebral disc to re-establish the height of the intervertebral space and the lordosis of the spinal segment, and more particularly to expansible vertebral implants of the intersomatic cage or corpectomy cage type.

To remedy certain pathologies, sometimes it is sought to obtain fusion of at least two adjacent vertebrae, for example when at least one of their adjacent intervertebral discs is lesioned.

From the prior art diverse arthrodesis techniques are known based on diverse types of implants, such as for example, intersomatic cages inserted into the place of a disc for re-establishing the height and the lordosis of the segment and for promoting bone growth (arthrodesis), to secure together two adjacent vertebrae.

Such devices are for example illustrated in French patent application FR1651637, which shows intersomatic cages giving the possibility of supplanting an intervertebral disc.

Further, to maximize the stability and graft volume contained in such implants and therefore the quality of the fusion, the latter have to cover a volume which is as close as possible to the volume occupied by the lesioned vertebral disc. The implants of the prior art therefore generally have a very large volume allowing their implantation relatively invasive for the patient.

One approach, used for reducing the size of the implants during their implantation and therefore their invasivity due to the necessary degradation during the route first, has been the use of expansible cages as for example described in European patent EP1699389 B1. Such cages, once they are implanted, are deployed by the surgeon, to cover a volume approaching the volume of an intervertebral disc, while having a profile allowing it to follow the lordosis of the vertebral column, thereby improving comfort for the patient and stability of the cage.

Nevertheless, this type of expansible cages includes a certain number of drawbacks. In particular, during their expansion, the surgeon has to exert an excessive pressure on the implant, notably because its expansion is simultaneously accomplished on two axes orthogonal with each other. Further, it is more difficult for the surgeon to observe a specific lordosis or to control the lordosis obtained. Finally, this type of implant does not rest or only very little on the cortical bone of the vertebra, but on a softer portion of the bone at the centre of the intervertebral space, which reduces its stability and has a risk of sinking.

In addition, for some devices disclosed in the prior art, the expansion of this type of cages is limited. Indeed, the final volume of the expanded cage is substantially identical to or a little greater than the initial volume.

Moreover, these implants often have a mechanism within the cage for allowing deployment. This mechanism occupies a significant portion of the graft space, and prevents the insertion of many grafts, which is detrimental to good fusion of the vertebrae.

SUMMARY OF THE DISCLOSURE

The object of the present application is therefore to propose an expansible intervertebral implant, for example of the intersomatic cage or corpectomy cage type, giving the possibility of overcoming at least one portion of the drawbacks of the prior art, by proposing an alternative implant having increased stability and reliability and easier expansion for surgeon, while observing the lordosis of the patient.

For this purpose, the application relates to an expansible intervertebral implant intended to be implanted in a space between two adjacent vertebrae to supplant at least partly an intervertebral disc. In various embodiments, such an intervertebral implant may be characterized in that said implant comprises:

- an elongated body along a longitudinal axis (X) comprised between a proximal end and a distal end, the latter being defined as being the end intended to penetrate first into said intervertebral space,
- at least one flexible arm mounted in the vicinity of the distal end of the longitudinal body, which may be moved between:
  - a folded-back position, in which said arm is positioned substantially parallel to the axis (X) and runs along the body,
  - a deployed position, in which said arm is not parallel to the axis (X) and away from the body to expand said implant along an axis (Y), by assuming the general shape of a circular arc,
- a means for deployment of said flexible arm for deploying the latter from the folded-back position to the deployed position, by the sliding of a proximal portion of said flexible arm with respect to the body inducing an increase in the space occupied by the implant, greater than the space of the implant in the folded-back position.

According to a special feature, said implant may be provided with one or several flexible arm pairs in nitinol.

According to a special feature, the arms of each of the pairs may be positioned on either side of the elongated body.

According to a special feature, said flexible arms of each pair may be positioned according to axial symmetry, along the axis (X).

According to a special feature, said flexible arm pairs may be made with a single piece of nitinol which crosses the body and for which both portions jut out from the body forming said arms.

According to a special feature, said implant may be provided with a means for locking said flexible arm in its deployed position.

According to a special feature, said longitudinal body along an axis (X) may comprise at least two sub-portions superposed on each other and bound together at least in proximity to the proximal end by at least one connecting means and/or one joint.

According to a special feature, the implant may comprise at its proximal end a base bound to both sub-portions of the longitudinal body, by said connecting means and/or said joint.

According to a special feature, each of said sub-portions may include at least one flexible arm.

According to a special feature, said implant may be provided with a means for expansion of the body along an axis (Z) substantially orthogonal to the axes (X) and (Y).

According to a special feature, the means for expansion of the body along the axis (Z), may move the distal ends of both sub-portions away from each other.

According to a special feature, said means for expansion of the longitudinal body comprises at least one lockable connecting rod in a deployed position when said implant is expanded along the axis (Z).

According to a special feature, once the implant is expanded in the axis (Z), the arms on a same side of the body (2) may cooperate with each other so as to be at least partly superposed, while remaining in contact.

According to a special feature, the longitudinal body may be provided with at least one aperture at its proximal end, said aperture being configured so as to form at least one passage for:
  at least one tool cooperating with:
    said deployment means of said at least one arm, for deploying the latter, at least from the folded-back position to the deployed position,
    and optionally, said means (3) for expansion of the distal end of the longitudinal body along an axis (Z) substantially orthogonal to the axes (X) and (Y),
  and/or
  at least one anchoring device (7) configured for securing said implant to the adjacent vertebrae (V1 and V2).

According to another embodiment, the expansible intervertebral implant intended to be implanted in a vertebral segment may comprise:
  an elongated body (2) along a longitudinal axis (X) comprised between a proximal end and a distal end, the latter being defined as being the end intended to penetrate first into said intervertebral space, said elongated body comprises at least two sub-portions superposed on each other (2a, 2b) and bound together at least in proximity to the proximal end by at least one connecting means and/or a joint (6),
  at least one flexible arm (21) on each of said sub-portions (2a, 2b) mounted in the vicinity of the distal end of the longitudinal body, which may be moved between:
    a folded-back position, in which said arm (21) is positioned substantially parallel to the axis (X) and runs along the body,
    a deployed position, in which said arm (21) is not parallel to the axis (X) and away from the body to expand said implant along an axis (Y), by assuming the general shape of a circular arc,
  a means for deployment of said flexible arm (21) for deploying the latter from the folded-back position to the deployed position,
  a means (3) for expansion of the body along an axis (Z) substantially orthogonal to the axes (X) and (Y).

It will be noted that the term "substantially" is regularly used in the present description, notably relating to a feature such as an orientation or a direction, so as to indicate that the relevant feature may in fact be slightly different and not be exactly as designated (for example, the expression "substantially perpendicular" should be interpreted as "at least approximately perpendicular" since it may be possible to select an orientation which is not exactly perpendicular to be able to nevertheless fulfill substantially the same function).

Further, terms like the term "substantially" used in the present application may also be interpreted as defining that a technical feature may be "in general" ("generally") and often "preferably", as indicated, but that other embodiments or configurations may be within the scope of the present disclosure. Thus, the terms such as "significantly", "substantially" or "approximately" used with reference to certain technical features may be omitted in the present application but it will be clear for one skilled in the art that the definitions of these technical features are not limited, even in the absence of such terms, may in fact only be limited functionally if the function targeted by the technical feature may be obtained by an approximately identical or similar feature.

Figure 1A:
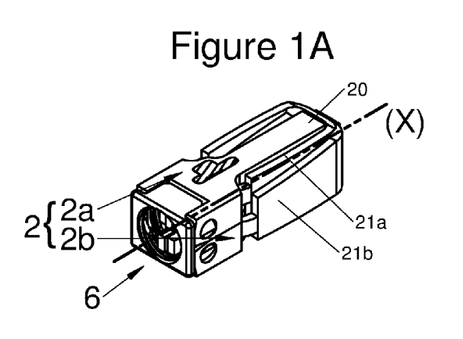
FIGS. 1A, 1B, and 1C are perspective illustrations of an embodiment of the implant with all its components in a first insertion configuration, then in a second configuration with the implant horizontally expanded, and finally in a third configuration with the implant expanded vertically, respectively.
Figure 1B:
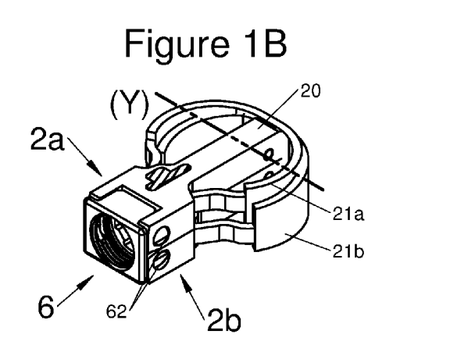

It should be noted that in this disclosure, reference will be made generally to a primary axis X, a secondary axis Y and a tertiary axis Z. The X, Y, and Z axes generally will be configured substantially orthogonal to each other, with the axis X corresponding to the direction along which an implant will travel during insertion into the patient, for example as depicted in FIG. 1A. In addition, generally references in this disclosure may contemplate that the primary axis X is a horizontal axis, the secondary axis Y is a lateral axis and the tertiary axis Z is a vertical axis considered with respect to the insertion path of an implant, but such directions are for ease of reference only and impose no limitations on the use, orientation, implantation, or other aspect of any embodiment within the scope of this disclosure. For example, in some preferred embodiments, the intervertebral implant 1 comprises a body 2 extending longitudinally along a primary axis X, between a proximal end and a distal end, so generally in this disclosure, the distal end may refer to the end by which the implant is introduced to the intervertebral space and the proximal end may refer to the end by which the implant is held during its implantation.

BRIEF DESCRIPTION OF THE SEVERAL VIEWS OF THE DRAWING

Other features, details and advantages of the object of the application will become apparent upon reading the description which follows with reference to the appended figures, in which the sets of FIGS. 1A to 1E, 2A to 2E, 3A to 3D, 4A to 4D, 5A to 5D, 6A to 6C and 7A to 7E, correspond to different illustrations of various embodiments of an implant described in the present application.

DETAILED DESCRIPTION OF VARIOUS EMBODIMENTS

Many combinations of the features of diverse embodiments may be contemplated without departing from the scope of the application; one skilled in the art will select one depending on the economic, ergonomic or dimensional constraints or other considerations which may be observable or applicable to a given deployment.

The sets of FIGS. 1A to 1E, 2A to 2E, 3A to 3D, 4A to 4D, 5A to 5D, 6A to 6C, and 7A to 7E depict various non-limiting embodiments of the present application. The various features of these embodiments may be mixed and combined in alternative more general embodiments, without any limitation. All of these embodiments include those not illustrated, and should be considered as fully within the scope of this disclosure. In addition, a person skilled in the art can possibly make use of the two other applications filed on the same day as the present application, by the same applicant, so as to ascertain possible functional and/or structural features which would be insufficiently detailed or not detailed in the present application. In other words, the entirety of these two other applications (description, claims and figures) can therefore be considered, if need be (depending on the applicable law), as being incorporated in the present application by reference.

More particularly, FIGS. 1A to 1D schematically illustrate the concept, object of the application, an intervertebral implant as a cage which expands horizontally and optionally vertically so that the volume occupied initially in the intervertebral space is less than the occupied volume in its final position of use. The distribution of the upper and lower contact areas of the implant with the vertebral endplates is then more reliable (balanced), i.e. the support on the periphery of the plates and the anterior portion are maximized since the cortical bone is denser therein at these localizations, thereby giving the possibility of better supporting the load and the implantation.

In various embodiments, the implant 1 comprises a body 2 of elongated shape along an axis X, with the body comprising a proximal end and a distal end. In some embodiments, the body 2 may comprise at least one flexible arm 21. In various embodiments, one or both ends of the flexible arm 21 may be pivotally mounted to the body 2 an pivot around a pivot axis 22 such as illustrated for example in FIGS. 5A to 5D, 6A to 6C, and 7A to 7D. In various embodiments, one or both ends of the flexible arm 21 may be slidably mounted to the body 22 using a loose attachment such as illustrated for example by orifices 220 depicted in FIGS. 1A to 1E and 2A to 2E or by lugs 211 depicted in FIGS. 3A to 3C. In various embodiments, one point of flexible arms 21 may be rigidly attached or integral with the body 2 such as illustrated for example in FIGS. 1A to 1F, 2A to 2E, 3A to 3C, and 4A to 4D. In various embodiments, the respective flexible arms 21 may be formed in one piece with portions disposed on opposite sides of the body 2, for example, such as illustrated for example in FIGS. 7A to 7E. In various embodiments, one or more different types of attachment means, such as those described herein, may be used in the same implant.

In other words, the implant 1 may comprise an elongated body 2 along an axis X, comprising a proximal end and a distal end. The distal end is often defined as the end which is first introduced into the intervertebral space, alternatively the proximal end is the one inserted last and also the one with which the implant is held. It will be noted that this conventional definition depends on the implantation route. Said body 2 may be provided with at least one flexible arm 21, which may be pivotally mounted 22, as illustrated in FIGS. 5A to 5D, in one piece with the body 2 or attached on the latter, without any hinge or joint, as shown in the other figures. The flexible arm moves between a folded-back position and at least one deployed position.

In the folded-back position, the arm 21 may be positioned along the body 2, close to or alongside, i.e. substantially parallel to the axis X to minimize the dimensions of the implant for its implantation in the patient, thus giving the possibility of reducing the invasiveness of the surgical operation. In certain embodiments, the arms 21 are juxtaposed against the body 2 when the implant is in the insertion configuration.

In the deployed position, i.e. the final position of use, a portion of the distal end 210 of the arm 21 slides along the body 2. The implant 1 is then deployed along an axis Y substantially perpendicular to the body 2, by the fact that the arm 21 is deformed so as to become arched. Thus, the implant occupies a larger space, while allowing increased stability and reliability, since the surface, in contact with the bone of the vertebrae, in particular the cortical bone is greater than in the folded-back position. In other words, the implant has gained in volume and in contact surface by the sliding of a portion of the distal end of the arm and by the deformation of the arm. This deformation may be elastic or plastic depending on the material making up the arm. This deployment is not a redistribution of the initial volume of the implant, but actually an increase in the latter.

Figure 1C:
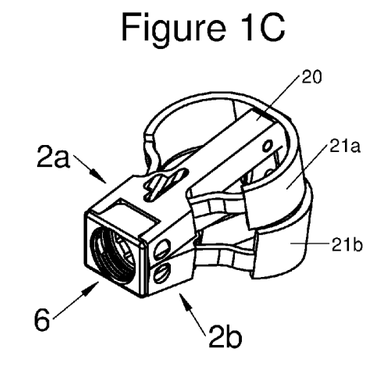
Figure 1D:
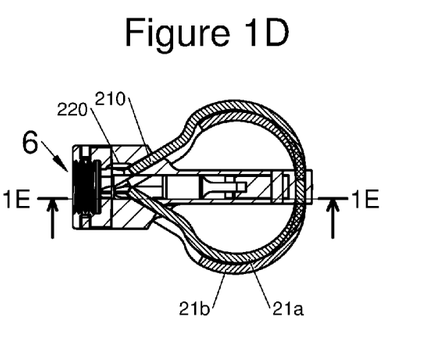
FIGS. 1D and 1E are respectively a longitudinal and transverse sectional view of the illustration of an embodiment of the implant illustrated by FIGS. 1A and 1C, along the plane 1D-1D of FIG. 1E and along the plane 1E-1E of FIG. 1D, respectively.
Figure 1E:
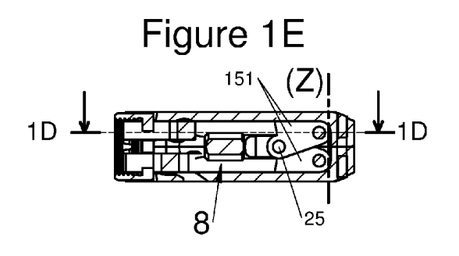
Figure 2A:
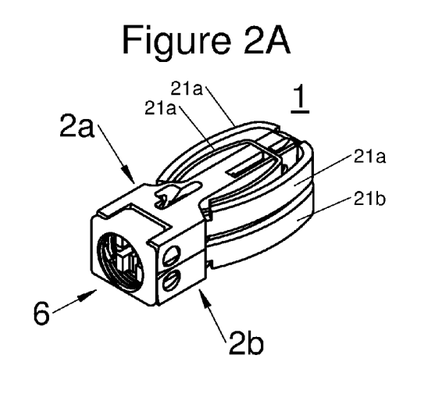
FIGS. 2A and 2B are perspective illustrations of an embodiment of an implant in an insertion configuration and in a deployed configuration, respectively.
Figure 2B:
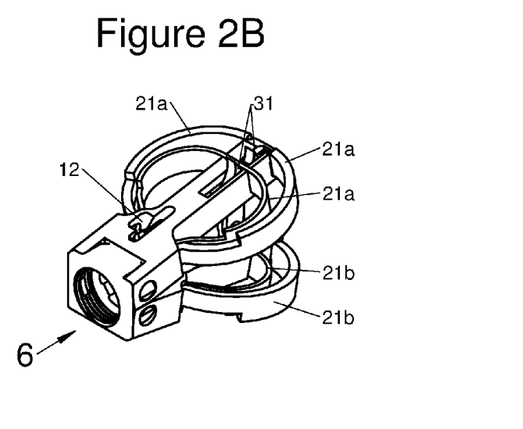
Figure 2C:
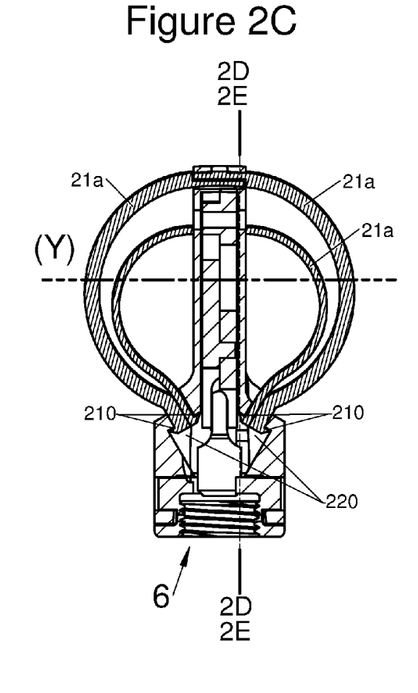
FIG. 2C is a sectional view along the plane 2C-2C of the embodiment of an implant illustrated by FIG. 2D, and FIGS. 2D and 2E are respectively a sectional view along the planes 2D-2D and 2E-2E of the embodiment of an implant illustrated by FIG. 2C.
Figure 3A:
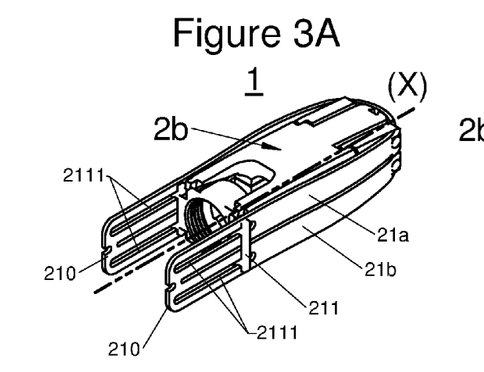
FIGS. 3A, 3B, and 3C are perspective illustrations of an embodiment of the implant with all components in an insertion configuration, with the implant horizontally expanded and with the implant horizontally and vertically expanded in a deployed configuration, respectively.
Figure 3B:
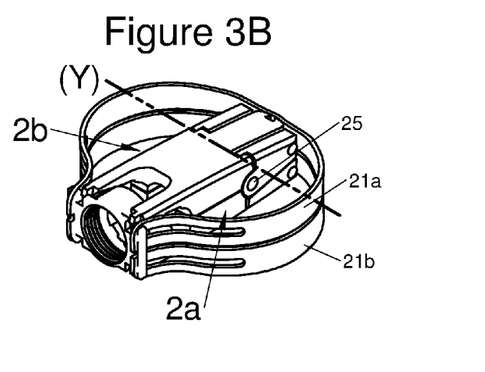
Figure 3C:
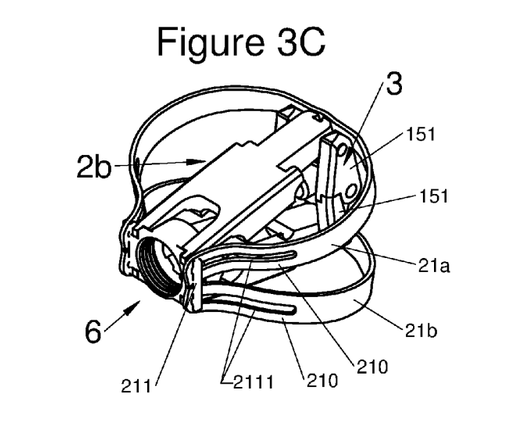
Figure 3D:
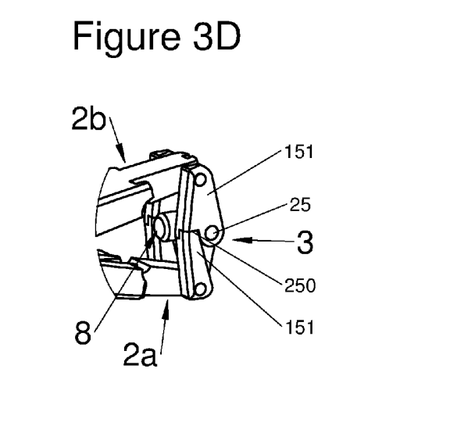
FIG. 3D illustrates a perspective view of expansion means when the arms of the implant are deployed.
Figure 4A:
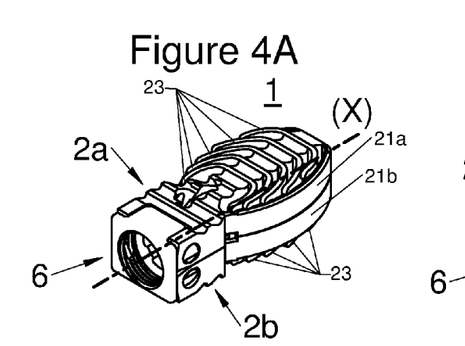
FIGS. 4A and 4B are perspective illustrations of an embodiment of the implant with all components in an insertion configuration and with the implant horizontally expanded, respectively.
Figure 4B:
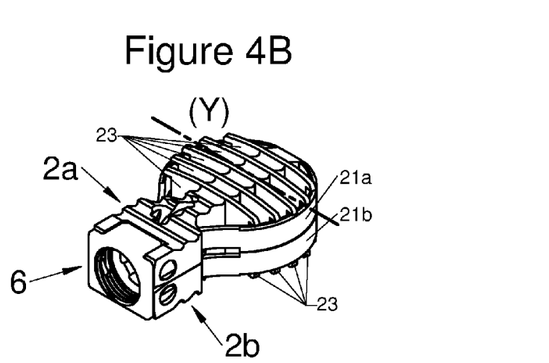
Figure 4C:
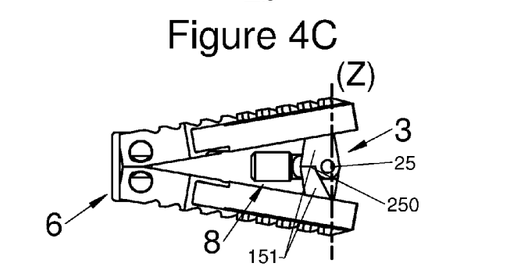
FIG. 4C is an illustration of the embodiment of FIGS. 4A and 4B in a configuration deployed vertically.
Figure 4D:
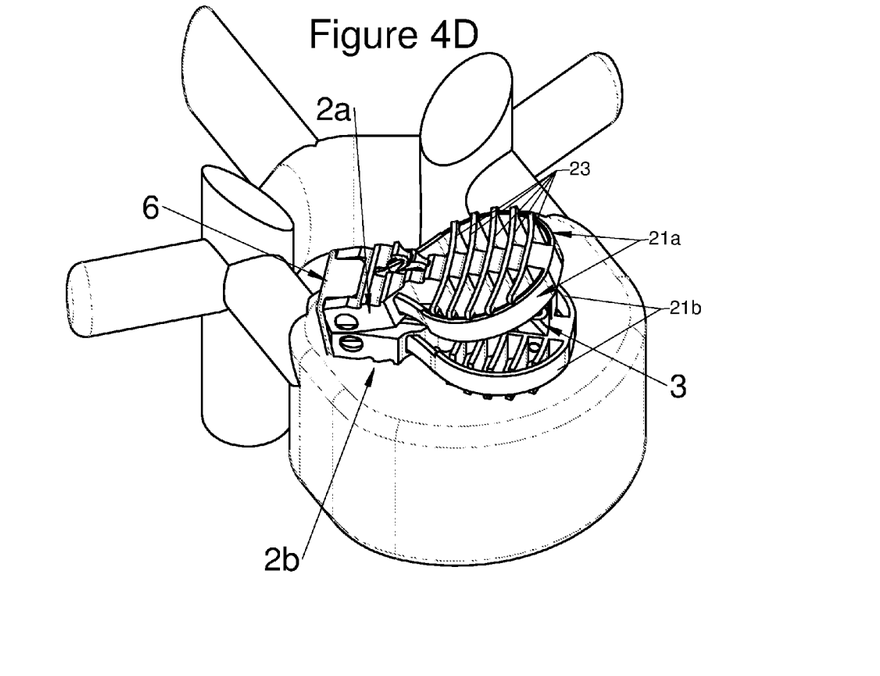
FIG. 4D is a perspective illustration of the embodiment of FIG. 4C disposed on a vertebra V.

According to various embodiments, a portion of the proximal end 210 of the arm 21 may be locked or retained in at least one deployed position, by locking means, for example the portion may be:

inserted and captured in at least one orifice 220 of the body, as shown for example in FIGS. 1D and 2C, or hooked-up to the body 2 via at least one retainer or catch element, as shown for example by a lug 211 in FIGS. 3A to 3C, or free, along the body 2, as shown in FIGS. 5A to 5D.

Figures 5A, 5B:
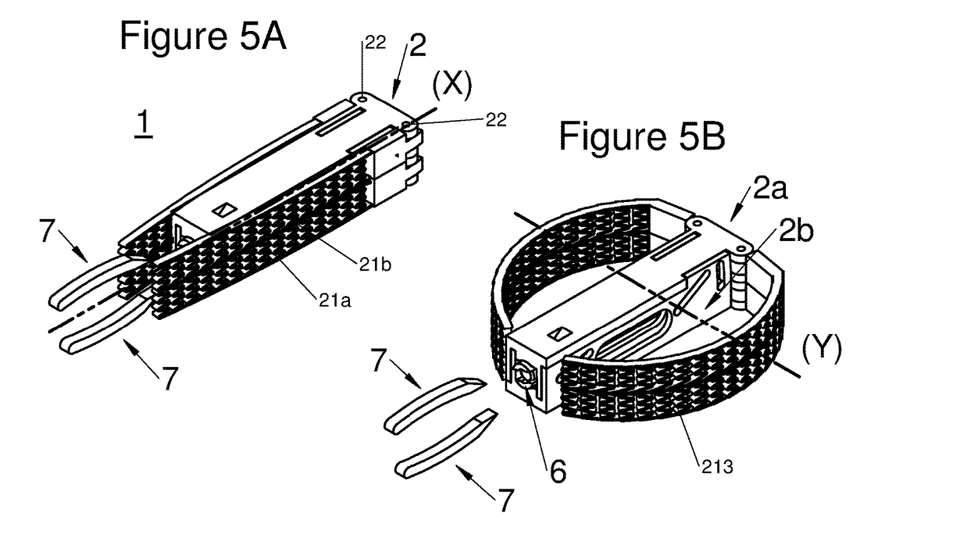
FIGS. 5A, 5B, and 5D are perspective illustrations of an embodiment of the implant with all components in an insertion configuration, with the implant horizontally expanded and with the implant horizontally and vertically expanded in a deployed configuration with anchors installed, respectively.
Figures 5C, 5D:
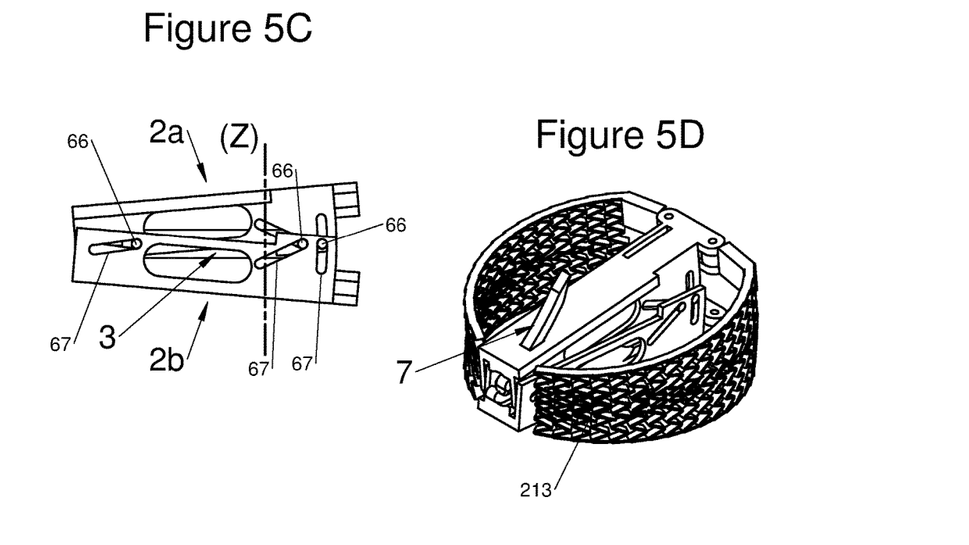
FIG. 5C is an illustration of a portion of the embodiment illustrated by FIG. 5B.

When the proximal end 210 of the arms 21 is free, the latter may be hooked-up or placed in proximity to the proximal end of the implant 1 to arch the flexible arms, for example as illustrated in FIGS. 5B and 5D.

Thus, according to various embodiments, the deployment of the implant may be adjustable, for example by means of several positions of the locking means (orifices 220/lug 211), or of several of the adjustable positions, for example, a screw or other control means which controls the sliding of the proximal end of the arm (not illustrated).

The implant 1 is provided with a means for deployment of said at least one arm from the folded-back position to the deployed position. This deployment means may have different shapes depending on the selected embodiment. However, its role is to reduce the distance between the proximal end of the arm and the distal end of the body to arch the arm, i.e. give it the general shape of a circular arc. This transformation may be achieved by means of sliding of a portion or "reserve" of the proximal end of the arm along the body. It is by handling this "reserve" of material (i.e. by totally or partly using it) that the practitioner expands more or less the implant, along the axis Y orthogonal to the body 2, to optimally occupy the intervertebral space depending on the morphology of each patient.

In various embodiments used, such as for example in the sets of FIGS. 1, 2 and 4, the locking means of the deployment may be achieved by shape cooperation between the orifice 220 and the proximal end 210 of the arm. The orifice 220 having such an adjusted configuration that the proximal end 210 cannot move within it without intervention of an external force. In some of these types of embodiments, the free end 210 may have an expanded profile, configured for example as a bulb or a lip as shown in FIG. 2C. In various other embodiments, such as for example in figure set 3 in which the locking means of the deployment is achieved by shape cooperation between the lug 211 and a groove 2111 in the proximal end 210 of the arm, for example using a friction fit to both retain the proximal end 210 to the body 2 and prevent movement of free end 210 when no external force is applied.

Figures 6A, 6B:
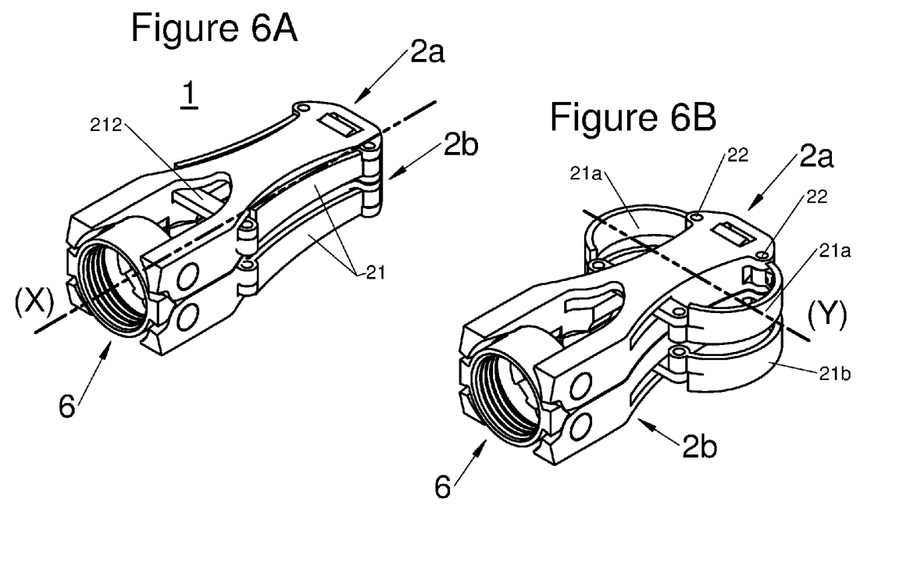
FIGS. 6A, 6B, and 6C are perspective illustrations of an embodiment of the implant with all components in an insertion configuration, with the implant horizontally expanded and with the implant horizontally and vertically expanded in a deployed configuration, respectively.
Figure 6C:
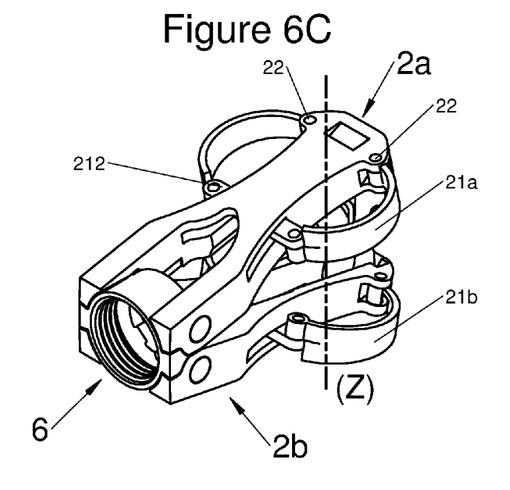

In various embodiments, for example as illustrated in the sets of FIGS. 6 and 7, a wedge 212 sliding along the axis X and crossing the body 2, allows deployment. When the wedge slides towards the distal end, the distance between the proximal end of the arm and the distal end of the body is found to be reduced, thereby allowing arching of the arm 21, as shown in FIGS. 6A and 6B. In this type of embodiment, the locking of the deployment may be obtained by immobilizing the wedge, for example by means of a screw, a lug or any type of abutment or other means of limiting movement of the wedge.

In various other embodiments, the arms 21 may be formed of a material having shape memory, with one position of the arm stable in the expanded state and locking means used to maintain the arms 21 in an insertion configuration, or may be formed of a material having a bistable shape memory, with arm positions that are stable both in the expensed state and in the insertion configuration.

According to diverse embodiments, said implant may be provided with locking means giving the possibility of locking the arm in its deployed position, this locking means may coincide with or be additional to the shape cooperation between the orifice 220 or the lug 211, and the reserve of the distal end of the arm.

In certain embodiments, the arm 21 may be made of a flexible material, for example nitinol. In some of these embodiments, the arm is stressed in the folded-back position. In other embodiments, it is in the folded-back position that the arm is at rest. Depending on the case, when the practitioner raises or adds at least partly the stress, the arm is released from the stress, allowing the latter to re-assume its deployed position or to be stressed to assume the deployed position and its arched shape as shown by FIGS. 1A-B, 2A-B, 3A-B, 4A-B, 5A-B, 6A-B, 7A-B.

In other words, in some of these embodiments, the arm may be stressed in the folded-back or insertion position and may have a tendency to assume the expanded or deployed position. In another of these embodiments, the arm may be stressed in the expanded or deployed position and may have a tendency to assume the folded-back or insertion position. In some other of these embodiments, the arm may exhibit bistability, and have a tendency to assume either the expanded or deployed position or the folded-back or insertion position. During deployment in many of these types of embodiments, force may be applied or removed to cause the arm to move from a stressed position to the stable position that the arm has a tendency to assume.

In various embodiments, such as for example illustrated by FIGS. 4A to 4D, fins 23 may be positioned along the body 2 of the implant. Such fins contribute to the deployment and to maintaining the flexible arms in their deployed position, in certain embodiments, the fins can, through shape memory or another spring action, help in the deployment and the retention in the deployed position of the flexible arms 21. In some of these embodiments, the fins are also in nitinol. These fins 23 may be also compressed along the body 2 by the flexible arms 21. These fins also allow generation of the contact surface with the vertebral bodies, thus said implant better resists the compression forces without however interfering with the occurrence of the fusion.

In various embodiments, examples of which are illustrated by the figures of the present application, said body 2 may preferably comprise at least one arm 21 in the vicinity of its distal end, i.e. the end which is the first in contact with the patient during the implantation of the implant.

In various embodiments, the implant may comprise an even number of arms 21, for example, 2, 4, 6, 8, 10, 12, 14, 16, 18, 20, 22 or further 24 preferably distributed symmetrically along the body 2 of the implant.

In various embodiments, each pair of arms may be made in a single piece 21 of nitinol, having the general shape of a strip, which crosses the longitudinal body of the implant along an axis orthogonal to the implant, the single piece of nitinol being secured to the body of the implant in its middle, to obtain on either side of the body two flexible arms 21*a* and 21*a* having substantially the same size and the same profile and two proximal ends 210. In other words and for the sake of understanding, it will then be considered that the free ends of the single piece 21 in nitinol are two proximal ends 210 and that the portions of the single piece in nitinol housed in the body are the distal ends. However, the arms 21*a* of each pair may be distinct and each attached on one side of the body 2.

Nevertheless, embodiments with an odd number of arms 21 are quite possible. In this case, it may be preferable that the arms be positioned alternately on either side of the body 2 of the implant, such as a zigzag.

In various preferred embodiments, the arms (e.g., 21, 21*a*, or 21*b*) comprise a strip-shaped portion, of flexible or resilient material, having opposing broad surfaces and edges connecting the opposing broad surfaces. Flexibility and/or resilience, preferably is limited to a bending deformation of the strip such that its longitudinal axis forms a curve in a plane perpendicular to a broad surface of the strip. Preferably, such strips are generally rigid in flexing, twisting or other deformations in other directions, including directions generally parallel to the broad surfaces of the strip. Such rigidity may enhance the ability of the implant to support the compressing forces imposed by the adjacent vertebrae.

Figure 7A:
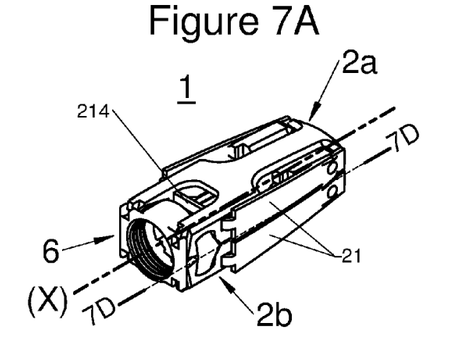
FIGS. 7A, 7B, and 7C are perspective illustrations of an embodiment of the implant with all components in an insertion configuration, with the implant horizontally expanded and with the implant horizontally and vertically expanded in a deployed configuration, respectively.
Figure 7B:
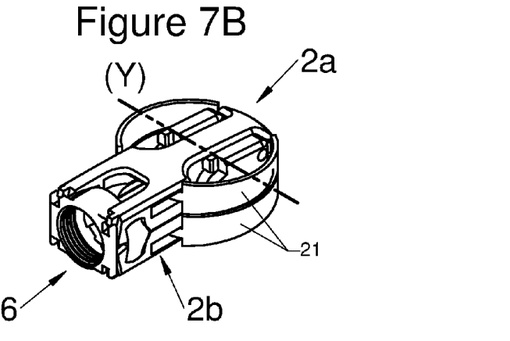
Figure 7C:
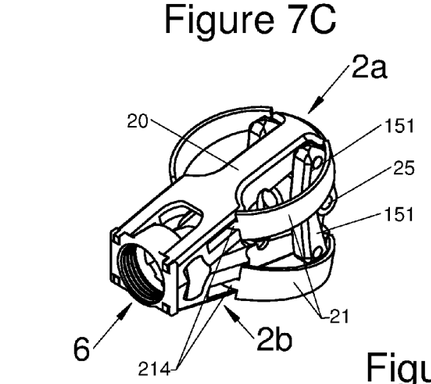
Figure 7D:
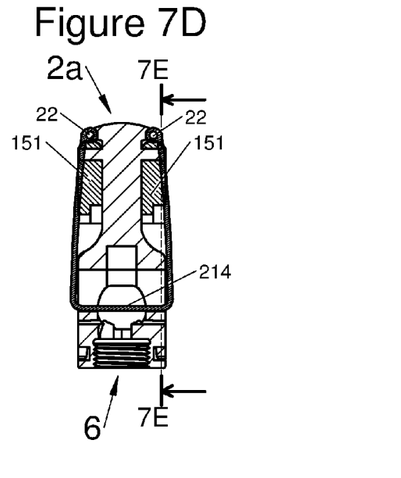
FIGS. 7D and 7E are respectively a longitudinal and transverse sectional view of embodiments illustrated by FIG. 7A along the plane 7D-7D and FIG. 7D along the plane 7E-7E, respectively.
Figure 7E:
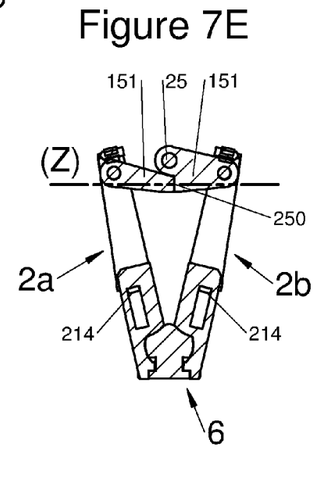

In various embodiments, illustrated for example by FIGS. 7A to 7E, the pair of arms 21 may comprise of a single piece of nitinol for which the free ends are pivotally mounted 22 on either side of the distal end of the body, as clearly shown in FIG. 7D. The middle of the single part of nitinol is then, in this configuration, not attached to the body 2, but sliding through the latter along the axis X. Such embodiments may have a deployment means comprising the central portion 214 of the single nitinol part forming the arm 21, with translation of this central portion 214 toward the distal end of the implant 1, to expand the arm 21 on each side of the body 2 during lateral deployment.

According to diverse embodiments, said longitudinal body may comprise two sub-portions 2a and 2b positioned on each other. Both sub-portions are generally bound together through at least one joint 6. Preferably, this joint is found at the proximal end of the body, i.e. on the side closest to the vertebral spines when said implant is implanted in a patient, via a posterior route. More specifically, this joint may give the possibility of binding a base to both sub-portions 2a and 2b. This is by this phase that the practitioner may hold the implant.

Said joint 6 allows a movement of both sub-portions 2a and 2b and in particular of their respective distal ends along an axis Z substantially orthogonal to the axes X and Y.

In diverse embodiments, said joint 6 may be provided with fins (not shown) which are deployed according to a movement following the axis Y. Such a deployment, gives the possibility of enlarging the volume occupied by the implant in the intervertebral space and promote stability of the latter. Moreover, these fins also give the possibility of better containing a graft inserted into the implant (in order to promote bone growth and arthrodesis) and of avoiding its migration towards the nerve roots or of the dura mater. Such fins may be in nitinol.

In certain embodiments, the implant 1 has means 3 for expanding the longitudinal body along an axis Z orthogonal to the axes X and Y. In particular said expansion means 3 allows the distal ends of the sub-portions 2a and 2b to move away from each other. Such a feature allows observance of the lordosis of the vertebral column. Further, the expansion along the axis Z may be modulated by the surgeon during the implantation so as to perfectly correspond to lordosis of the patient.

According to diverse embodiments, the expansion means may, depending on the embodiments, include:

At least one scissor lift structure or a small connecting rod formed for example with arms 151 and with an axis 25 having preferably at least a locking position, for example by means of shape cooperation 250 of the arms 151. This small connecting rod, in various embodiments, may also comprise an abutment 8, which may be provided with a thread, which cooperates with a tool held by the practitioner to facilitate deployment of the implant along the axis Z.

At least one wedge. This wedge 3 according to the embodiments, slides along the body 2 in at least one guide 67 having a mating shape with a portion 66 of the wedge 3.

Further, when the implant expands along the axis Y and Z, the expansions may be:

sequential, for example a first expansion along the axis Y, and then a second expansion along the axis Z or further a first expansion along the axis Z, followed by a second expansion along the axis Y, or simultaneous, i.e. the expansion along the axis Y is concurrent with the expansion along the axis Z.

In various embodiments, nevertheless without being limiting, a sequential expansion beginning with the axis Y may be preferred. Indeed, due to the stresses on the vertebrae and on the vertebral column generally, it may be easier to perform an expansion along the axis Y than an expansion along the axis Z and the expansion along the axis Y may be better informed if the implant has not yet expanded in height.

In embodiments, the arms 21 may be provided with a structure 213 allowing their extension along an axis substantially parallel to the axis Z, for example a meshing compressed beforehand, as illustrated by the set of FIGS. 5A to 5D or a structure of the accordion/fan type. Thus, with such structures, the compression forces which are undergone by the implant are distributed on the whole of the latter, reinforcing its stability. These flexible extensions further give the possibility of restricting the access to the graft space by the sides of the implant and of well containing the graft which will subsequently be injected within the implant.

In embodiments, the arms 21a and 21b on a same side of the body 2 may have a complementary profile between them so that they superpose, at least partly, while remaining in contact when the implant is deployed in the axis Z, as shown by FIG. 1C. Thus, the stability of the implant is reinforced. In certain embodiments, the curvature of the arms may be asymmetrical so that only one portion of the upper arm 21a rests on a portion of the lower arm 21b. Such a configuration gives the possibility of enlarging the space occupied by the arms and thus gives the possibility of better distribution of the stresses and therefore improves the stability of the implant.

In embodiments, said longitudinal body may be preferably provided with an aperture at its proximal end, to let through a tool actuating said deployment means of said at least one arm, (in order to move said arm from the folded-back position to the deployed position), and/or, said expansion means of the distal end of the longitudinal body along an axis Z orthogonal to the axes X and Y, and/or let through at least one anchor or anchoring device 7 configured for securing the implant to the adjacent vertebrae (V). Further, the aperture allows introduction of a graft to promote bone growth and thereby reinforce the stability of the implant. In certain embodiments, the aperture may be formed by the profile of both sub-portions 2a and 2b of the body, or have in the base which comprises at least one joint 6, allowing expansion of the distal end of the body along the axis Z.

Figure 2D:
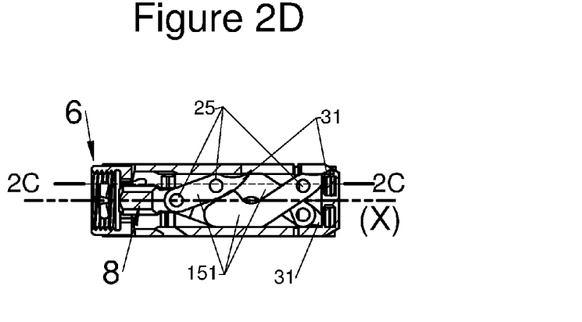
Figure 2E:
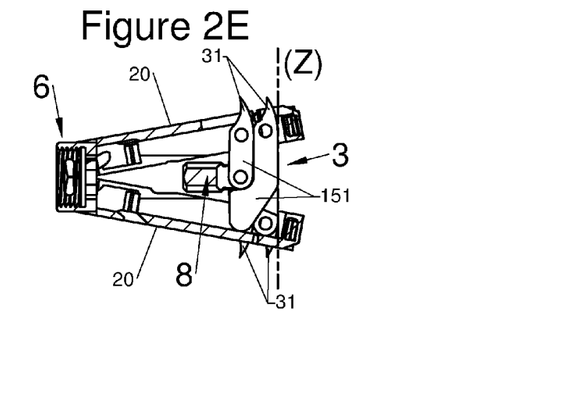

In embodiments, the anchoring device 7 may be replaced or complemented by anchors 31 integrated to the expansion means 3, in particular when the latter is a small connecting rod, for example as shown in FIGS. 2D and 2E.

In embodiments, the implants are provided with apertures, for example right through, to promote bone growth in their inside. These apertures thus give the possibility of reinforcing the anchoring and the stability of the implant, in the long run, by arthrodesis.

Further, regardless of the embodiment, the arm may comprise on the surfaces in contact with the bone, a profile promoting the frictional forces, such as of teeth, notches or other irregularities, to guarantee the maintaining of the arm in its deployed position.

It will easily be understood upon reading the present application that the particularities of the present application, as generally described and illustrated in the figures, may be arranged and designed according to a great variety of different configurations. Thus, the description of the present application and the relating figures are not provided for limiting the scope of the application but simply illustrate selected embodiments.

One skilled in the art will understand that the technical characteristics of a given embodiment may in fact be combined with characteristics of another embodiment unless the opposite is explicitly mentioned or unless it is obvious that these characteristics are incompatible. Further, the technical features described in a given embodiment may be isolated from the other features of that embodiment unless the opposite is explicitly mentioned. In particular, the embodiments described in the present application, although they are detailed with reference to illustrative and non-limiting figures, in which the implant may be designed for a posterior approach implantation, are not limited to a particular vertebral level or to a particular implantation route. It is therefore clear that these features could be adapted to a cervical, or lumbar implantation, and by the different routes of traditional approaches (anterior, posterior, lateral etc.). The arrangement of the various components of the implant is then modified to allow such an implantation, and so that the expansion of the implant is suited to its position in the spine and complying with the configuration of the latter. For example, in the case of an implantation by an anterior route, it may be easily possible to consider having a gripping means of the implant allowing said implant to be held at its distal end (i.e. the end opposite to the joint 6), and allowing actuation of the deployment means, preferably thanks to a traction, to expand the cage in one or two dimensions.

It should be obvious for those skilled in the art that the present application allows embodiments under many other specific forms without departing from the field defined by the scope of the appended claims, they should be considered as an illustration and the application should not be limited to the details given above.

The invention claimed is:

1. An expansible intervertebral implant comprising:
   a body elongated along a longitudinal axis extending between a proximal end and a distal end;
   a first arm that is flexible and that is mounted proximal to the distal end, the first arm movable between
      a retracted position in which the first arm is positioned along the body and substantially parallel to the longitudinal axis, and
      a deployed position in which the first arm extends along a lateral axis angularly disposed to the longitudinal axis and away from the body, forming the implant into a general shape of a circular arc;
   a plurality of superposed subportions bound together proximal to the proximal end of the body by a connector; and
   an actuator operable to move the first arm from the retracted position to the deployed position by sliding a proximal portion of the first arm with respect to the body.

2. The expansible intervertebral implant according to claim 1, in which the first arm comprises nitinol.

3. The expansible intervertebral implant according to claim 1 further comprising a second arm positioned on an opposite side of the body from the first arm.

4. The expansible intervertebral implant according to claim 3 in which the first arm and the second arm are symmetrically positioned along the longitudinal axis.

5. The expansible intervertebral implant according to claim 3 in which the first arm and the second arm are made with a single piece of nitinol which crosses the body juts out from the body forming the first and second arms.

6. The expansible intervertebral implant according to claim 1 further comprising a lock operable to retain the first arm in the deployed position.

7. The expansible intervertebral implant according to claim 1 in which the implant comprises at the proximal end a base bound to the plural subportions by the joint.

8. The expansible intervertebral implant according to claim 7 in which each of the subportions comprises a flexible arm.

9. The expansible intervertebral implant according to claim 8 in which the implant comprises an expander configured to expand the implant in the direction of a vertical axis oriented angularly to the longitudinal axis and the lateral axis.

10. The expansible intervertebral implant according to claim 9 in which the expander is operable to move distal ends of the subportions apart.

11. The expansible intervertebral implant according to claim 10 in which the expander comprises a connecting rod operable to lock the implant expanded along the vertical axis.

12. The expansible intervertebral implant according to claim 9 in which the body comprises an aperture at its proximal end configured to form a passage for a tool for operating the actuator.

13. The expansible intervertebral implant according to claim 12 in which the passage accommodates a tool for operating the expander.

14. The expansible intervertebral implant according to claim 13 in which the passage is configured for insertion of an anchor into the intervertebral implant.

15. An expansible intervertebral implant comprising:
   a body elongated along a longitudinal axis between a proximal end and a distal end and comprising
   plural subportions that are superposed and bound together proximal to the proximal end by a connector;
   a flexible arm disposed on each of the subportions and mounted in the vicinity of the distal end of the body, each flexible arm movable between
      a folded-back position in which said arm is positioned substantially parallel to the longitudinal axis and along the body, and
      a deployed position in which said arm is oriented angularly to the longitudinal axis and away from the body and formed into the general shape of a circular arc to expand the implant along a lateral axis;
   means for deployment of each flexible arm from the folded-back position to the deployed position; and
   means for expanding the body along a vertical axis oriented angularly to the longitudinal axis and the lateral axes.

* * * * *